United States Patent
Veselovsky et al.

(10) Patent No.: US 11,311,639 B2
(45) Date of Patent: Apr. 26, 2022

(54) METHOD AND APPARATUS FOR CONTROLLING STERILIZATION CHAMBERS

(71) Applicant: Konnexis Inc., Kanata (CA)

(72) Inventors: Peter Veselovsky, Kanata (CA); Michael Omatsu, Ottawa (CA); Ahmad Juqqa, Ottawa (CA); Nader Hijazi, Ottawa (CA)

(73) Assignee: Konnexis Inc., Kanata (CA)

( * ) Notice: Subject to any disclaimer, the term of this patent is extended or adjusted under 35 U.S.C. 154(b) by 0 days.

(21) Appl. No.: 16/597,162

(22) Filed: Oct. 9, 2019

(65) Prior Publication Data

US 2020/0038532 A1 Feb. 6, 2020

Related U.S. Application Data

(63) Continuation of application No. 15/297,816, filed on Oct. 19, 2016, now Pat. No. 10,441,673.

(51) Int. Cl.

| | |
|---|---|
| *G11B 11/00* | (2006.01) |
| *G05B 15/00* | (2006.01) |
| *G06F 17/00* | (2019.01) |
| *A61L 2/24* | (2006.01) |
| *A61L 2/20* | (2006.01) |
| *G06F 3/0482* | (2013.01) |

(52) U.S. Cl.
CPC ............... *A61L 2/24* (2013.01); *A61L 2/206* (2013.01); *G06F 17/00* (2013.01); *A61L 2202/14* (2013.01); *G06F 3/0482* (2013.01)

(58) Field of Classification Search
CPC .......... A61L 2/00; A61L 2/0094; A61L 2/206; G06F 7/00; G06F 9/00; G06N 3/00; G06N 5/00
USPC ....... 422/28, 62, 105, 119; 700/1, 90; 701/1, 701/85, 127; 340/1.1, 407.2; 369/13.01
See application file for complete search history.

(56) References Cited

U.S. PATENT DOCUMENTS

| | | | |
|---|---|---|---|
| 2003/0083902 A1* | 5/2003 | Hehenberger | ..... G06Q 30/0601 705/2 |
| 2009/0257912 A1 | 10/2009 | Lane et al. | |

FOREIGN PATENT DOCUMENTS

| | | | |
|---|---|---|---|
| EP | 0750914 A1 | 1/1997 | |
| EP | 1725161 B1 * | 1/2010 | ............... A61B 1/12 |
| WO | 2013181387 A1 | 12/2013 | |
| WO | 2015049002 A1 | 4/2015 | |

OTHER PUBLICATIONS

Extended European Search Report in application No. 17194696.5, dated Mar. 21, 2018.

* cited by examiner

*Primary Examiner* — Monzer R Chorbaji
(74) *Attorney, Agent, or Firm* — Moffat & Co

(57) ABSTRACT

There is provided a method and apparatus for operating a sterilization chamber such that one version of Programmable Logic Controller (PLC) software is compatible with any number of hardware configurations of the sterilization chamber. The PLC software is divided into a core module for operations which are the same across all hardware configurations, and a template module for hardware specific operations. Configuration data, state data, and live data are segregated from each other.

15 Claims, 10 Drawing Sheets

METHOD AND APPARATUS FOR CONTROLLING STERILIZATION CHAMBERS

FIELD OF THE DISCLOSURE

The present disclosure relates to sterilization chambers, and in particular to a method of controlling multiple sterilization chambers having different hardware configurations with a single program.

BACKGROUND

Sterilization chambers are used to sterilize product, such as medical devices, on a very large scale. Such chambers are typically controlled by a Programmable Logic Controller (PLC).

A sterilization cycle is defined by a sequence of phases to be performed by the chamber. For example, phases may involve operations like injecting or removing gases like steam, nitrogen, Ethylene Oxide (EtO), or air from the chamber, at specific pressures, rates, temperatures, and for specific time periods. These operations are performed by devices of the chamber, such as a valve, or a pump, and feedback from the chamber environment is obtained through sensors such as temperature or pressure sensors. Different devices and sensors may be attached to each chamber and each such hardware configuration may be controlled and monitored using a specific version of control software.

To ensure proper sterilization of the product, the sterilization cycles have to be performed consistently with a high degree of confidence. However, when an operator has chambers from different manufacturers, having a variety of sizes and hardware configurations, it becomes more and more difficult to ensure quality control across all chambers.

Over time, features may be added or removed, creating further software versions that need to be maintained for every type of chamber.

Furthermore, with each chamber running its own custom program, debugging becomes much more difficult and labor intensive. Each chamber program needs to be maintained separately, and a software upgrade on one chamber may affect other chambers differently, require testing for every chamber.

Since the PLC control program for each chamber typically combines configuration data, state chamber information, and program code in the same memory area, new program code may not be downloaded without overwriting and consequently losing configuration data and state chamber information. This applies especially if the memory structure, of the new software version, is different from the old version. This is typically overcome by having a developer implement each program code update in each chamber PLC manually.

The present disclosure provides methods and apparatus to overcome these and other deficiencies.

SUMMARY

One aspect of the present disclosure provides a method of operating a sterilization chamber from a computing device, comprising receiving configuration data for the chamber at the computing device, the configuration data indicating the hardware configuration of the sterilization chamber; reading phase information from a sterilization cycle specification; and invoking a subsystem of the sterilization chamber corresponding to the phase information using a standard interface of the subsystem; wherein the subsystem executes a phase using the phase information and the configuration data.

Another aspect of the present disclosure provides a computing device for operating a sterilization chamber, comprising a processor, memory, and a communication subsystem; wherein the processor, memory, and communication subsystem cooperate to receive configuration data for the chamber at the computing device, the configuration data indicating the hardware configuration of the sterilization chamber; read phase information from a sterilization cycle specification; and invoke a subsystem of the sterilization chamber corresponding to the phase information using a standard interface of the subsystem; wherein the subsystem executes a phase using the phase information and the configuration data.

Yet another aspect of the present disclosure provides a non-transitory computer-readable medium having executable code stored thereon for execution by a processor of a computing device for operating a sterilization chamber, the executable code comprising instructions for receiving configuration data for the chamber at the computing device, the configuration data indicating the hardware configuration of the sterilization chamber; reading phase information from a sterilization cycle specification; and invoking a subsystem of the sterilization chamber corresponding to the phase information using a standard interface of the subsystem; wherein the subsystem executes a phase using the phase information and the configuration data.

DETAILED DESCRIPTION

Figure 1:
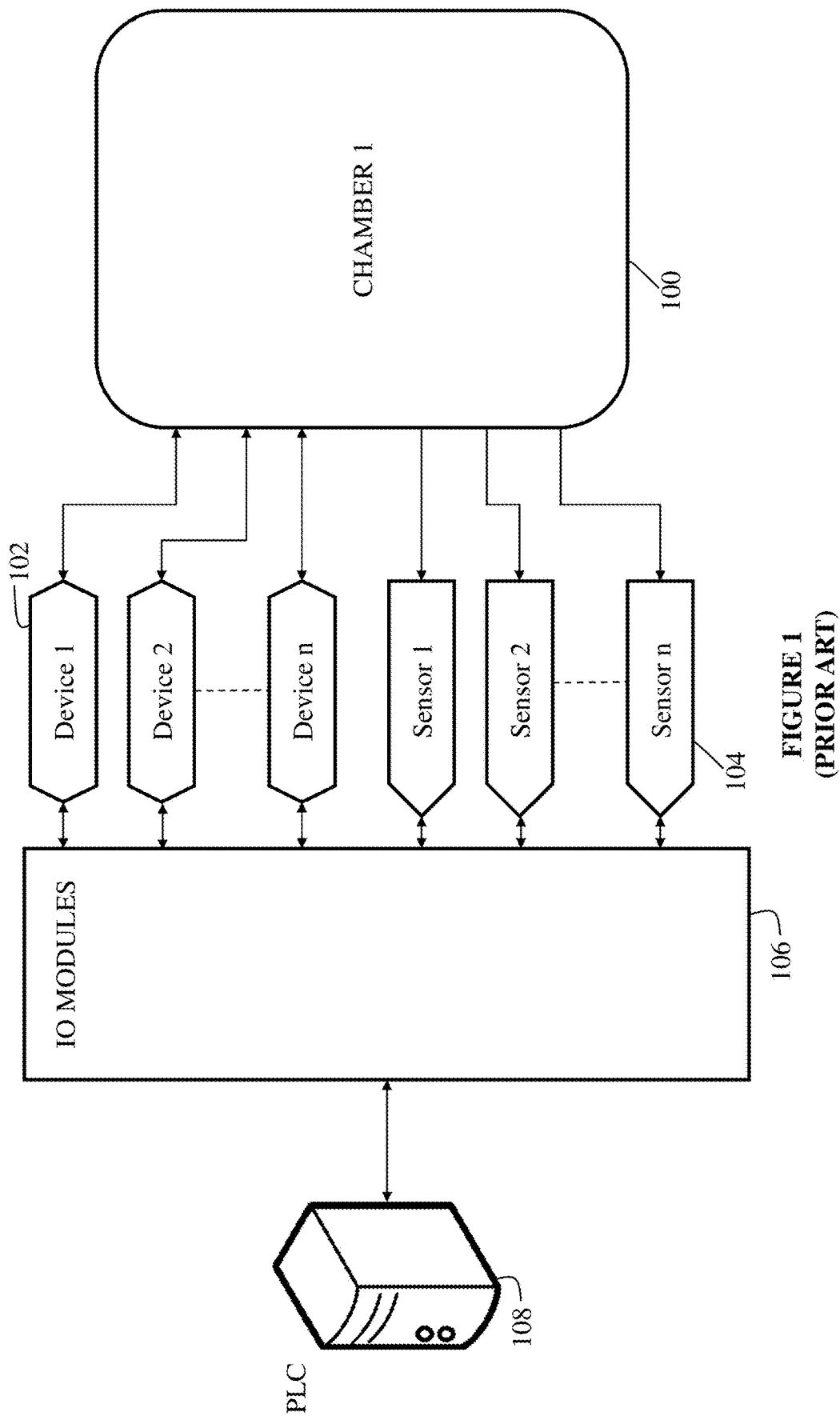
FIG. 1 is a conceptual diagram of a sterilization chamber according to the prior art.

A conventional sterilization chamber is shown with reference to FIG. 1. Such a chamber may be an Ethylene Oxide (EtO) chamber, for sterilizing medical product, but the present disclosure is not so limited, and other types of chambers may be controlled according to the present disclosure.

A chamber 100 is equipped with a plurality of devices and sensors. As shown in FIG. 1, a plurality of devices 102 actuated by the PLC 108 via the 10 modules 106 control the environment within chamber 100, to effect a sterilization cycle. Devices 102 may comprise valves, pumps, heating elements, and the like, however, the present disclosure is not limited to any particular configuration of devices.

Also shown in FIG. 1, a plurality of sensors 104 communicate with the chamber and IO modules 106. The sensors 104 provide readings of the conditions inside the chamber, to ensure that the sterilization cycle is executed as designed. Sensors 104 may comprise pressure sensors, temperature sensors, humidity sensors, and the like, however the present disclosure is not limited to any particular configuration of sensors.

Also shown in FIG. 1, a Programmable Logic Controller (PLC) 108 communicates with input/output modules 106 to interact with devices 102 and sensors 104.

During operation, the PLC 108 runs an executable program for chamber 100. The program directs the chamber to perform a sterilization cycle by controlling devices 102 and by reading data from sensors 104. During execution, PLC 108 also maintains state information, so that it is aware of what part of the sterilization cycle is happening at any given time. This information allows to resume a sterilization cycle that was interrupted.

Figure 2:
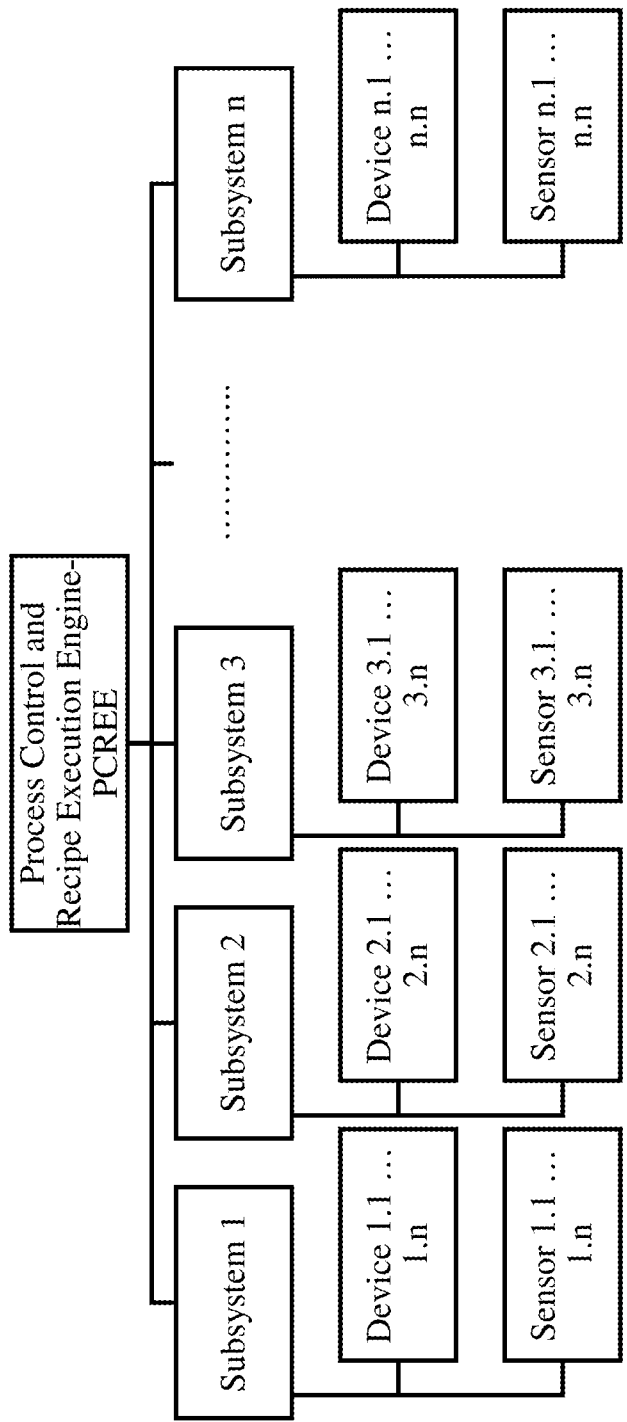
FIG. 2 is a conceptual diagram of a program structure for controlling a sterilization chamber according to the prior art.

A traditional program structure for the program executed by PLC 108 is shown with regard to FIG. 2. As seen in FIG. 2, the program is divided in two main blocks, the Process Control and Recipe Execution Engine (PCREE), and the Subsystem Modules.

The PCREE is responsible for executing the sterilization cycle, moving it from one phase to the next. In each phase a specific task is accomplished such as introducing a specific gas at a specific rate into the chamber. Each phase has end conditions associated therewith, and a phase ends when the conditions inside the chamber correspond to the end conditions. During a phase, the conditions inside the chamber change as a result of the operation of devices by the subsystems.

Subsystem modules are responsible for controlling how each phase is performed, how each specific task within a phase is accomplished, and how conditions inside the chamber are measured. For example, a subsystem module may be responsible for controlling how the specific gas is introduced in the chamber at the specific rate, until a specific pressure is achieved. This may be accomplished by opening and closing valves of the chamber, and taking readings from various sensors.

The subsystem modules are programmed to be specific to the type of hardware configurations that have been supplied with a chamber.

The above is further described with reference to FIG. 3.

Figure 3:
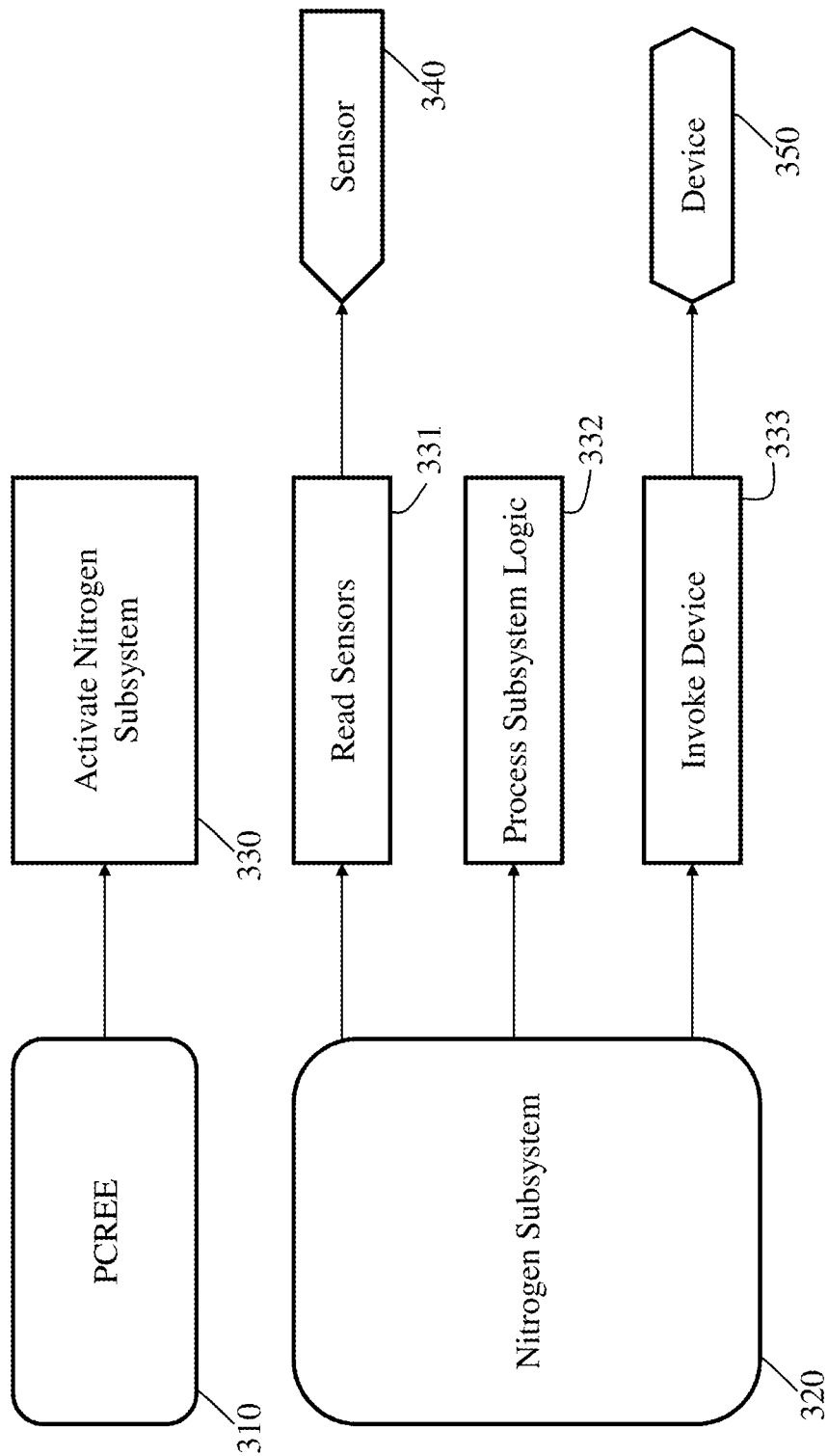
FIG. 3 is a conceptual diagram of a program flow for controlling a sterilization chamber according to the prior art.

As seen in FIG. 3, the PCREE 310 is controlling the execution of a sterilization cycle at a high level. In the example of FIG. 3, PCREE 310 is activating the Nitrogen Subsystem 320 at block 330. Nitrogen Subsystem 320 is only provided as an example, and other subsystems are regularly invoked by PCREE 310 during the execution of a sterilization cycle. For the purposes of this example, Nitrogen Subsystem 320 is the subsystem responsible for controlling the level of nitrogen in the sterilization chamber.

Nitrogen Subsystem 320 then performs its task by first reading sensor 340 at block 331, processing subsystem logic at block 332, and then by invoking device 350 at block 333.

As seen above, according to the prior art, the PCREE must be designed with each subsystem in consideration, and each subsystem must be designed with each device and sensor in consideration.

According to the present disclosure, a method of operating a sterilization chamber is provided which allows a single program to control any chamber, regardless of its manufacturer or model. This allows for consistent sterilization operation for each chamber, and for each sterilization cycle specification to be managed in a consistent manner and to be transferrable between chambers. The method of the present disclosure further allows for process state restoration following a catastrophic failure of the PLC, as will be described in greater detail below.

These objectives are achieved by the abstraction of chambers, subsystems and devices into configurable building blocks, the separation of configuration data, state data, and live data, and by the separation of software into configurable blocks.

Figure 4:
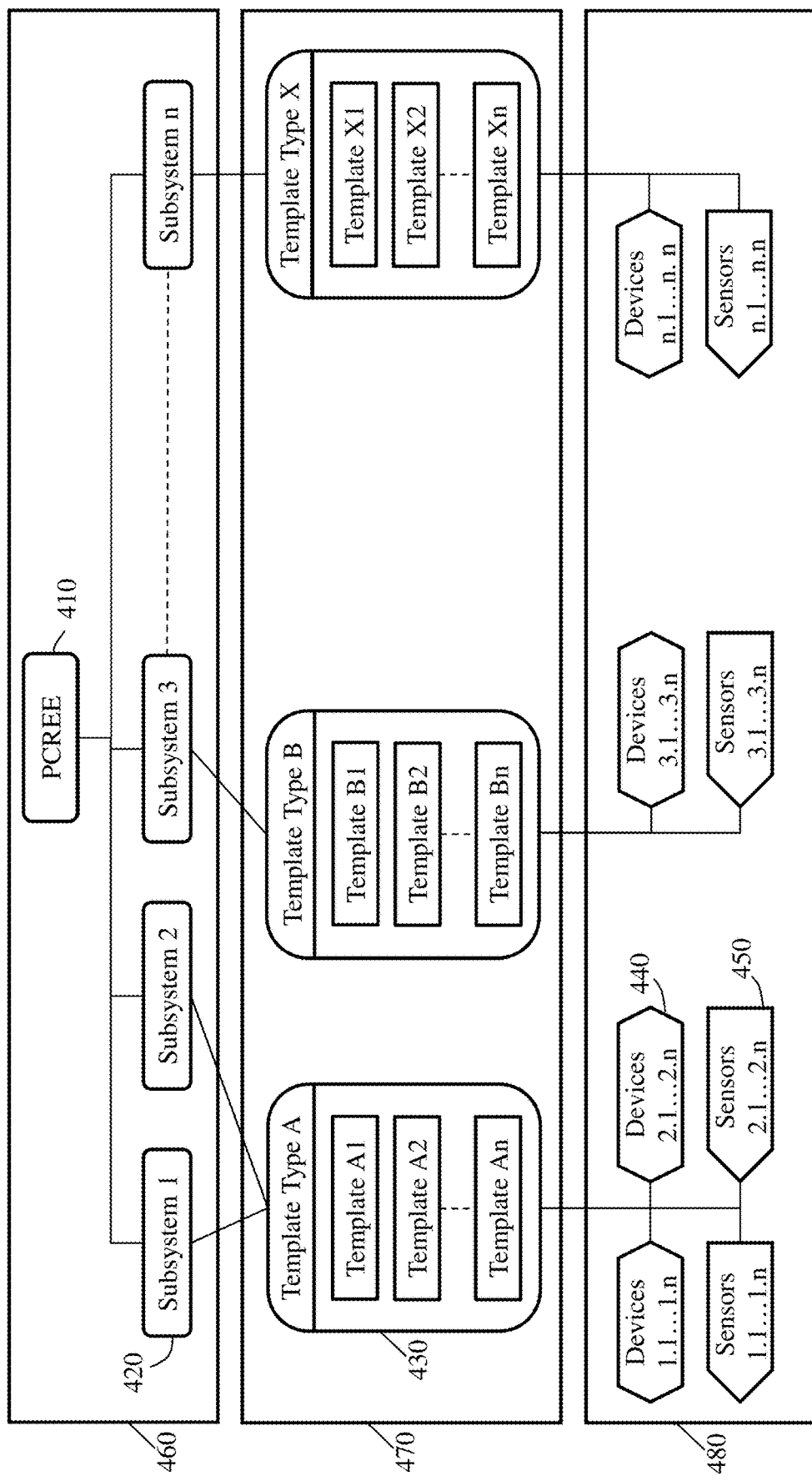
FIG. 4 is a conceptual diagram of a program structure according to at least one embodiment of the present disclosure.

Reference is now made to FIG. 4, in which a program structure according to one embodiment of the present disclosure is illustrated.

In FIG. 4, PCREE 410 invokes subsystems 420 to control the execution of a sterilization cycle at a high level. This is done in a standard manner, and the interface between the PCREE 410 and the subsystems 420 is also standard. This enables the same version of PCREE 410 to be usable across any chamber, regardless of the chamber's manufacturer or model.

More specifically, in the embodiment of FIG. 4, PCREE 410 embodies high-level functions which are the same for all sterilization chambers. For example, PCREE 410 may include functions such as reading the specifications of a sterilization cycle from a file, and invoking the appropriate subsystems in accordance with the sterilization cycle.

PCREE 410 and the standard interface to subsystems 420 are grouped together in FIG. 4 as Core Main Module 460. Each subsystem may have its own standard interface, so that PCREE 410 is capable of invoking each subsystem, regardless of the implementation details of each subsystem.

As further shown in FIG. 4, each subsystem 420 corresponds to one Template Type 430. Specifically, subsystems 1 and 2 correspond to Template Type A, subsystem 3 corresponds to Template Type B, and subsystem n corresponds to Template Type X. This configuration is merely provided as an example and is not limiting to the present disclosure.

Each template type contains a plurality of templates. In the example of FIG. 4, Template Type A includes Template A1, Template A2, . . . , and Template An, Template Type B includes Template B1, Template B2, . . . , and Template Bn, and Template Type X includes Template X1, Template X2, . . . , and Template Xn. Notably, the index 'n' of FIG. 4 is merely provided to illustrate that the number of templates is variable, and the use of 'n' in more than one instance does not suggest that the value of 'n' is the same across all instances.

Template type modules provide software for controlling specific hardware configurations. Each template type contains multiple hardware templates, one for each type of hardware configuration. Templates are selected or configured to match the hardware for a given chamber. For each Template Type 430, one template corresponding to the specific hardware of the chamber is selected. When a corresponding subsystem is activated by PCREE 410, the subsystem interfaces with a Template Type 430 using a standard interface, and Template Type 430 invokes the specific template corresponding to the specific hardware configuration for the chamber. The configuration of templates will be described in greater detail below.

As seen in FIG. 4, Template Types 430 are provided in Template Module 470, which is distinct from Core Main Module 460.

Template Module 470 then interfaces with Core Devices Module 480. Core Devices Module 480 provides generic methods executed on devices 440 and sensors 450. Each subsystem 420 is responsible for operation of a number of devices 440 and sensors 450.

Figure 5:
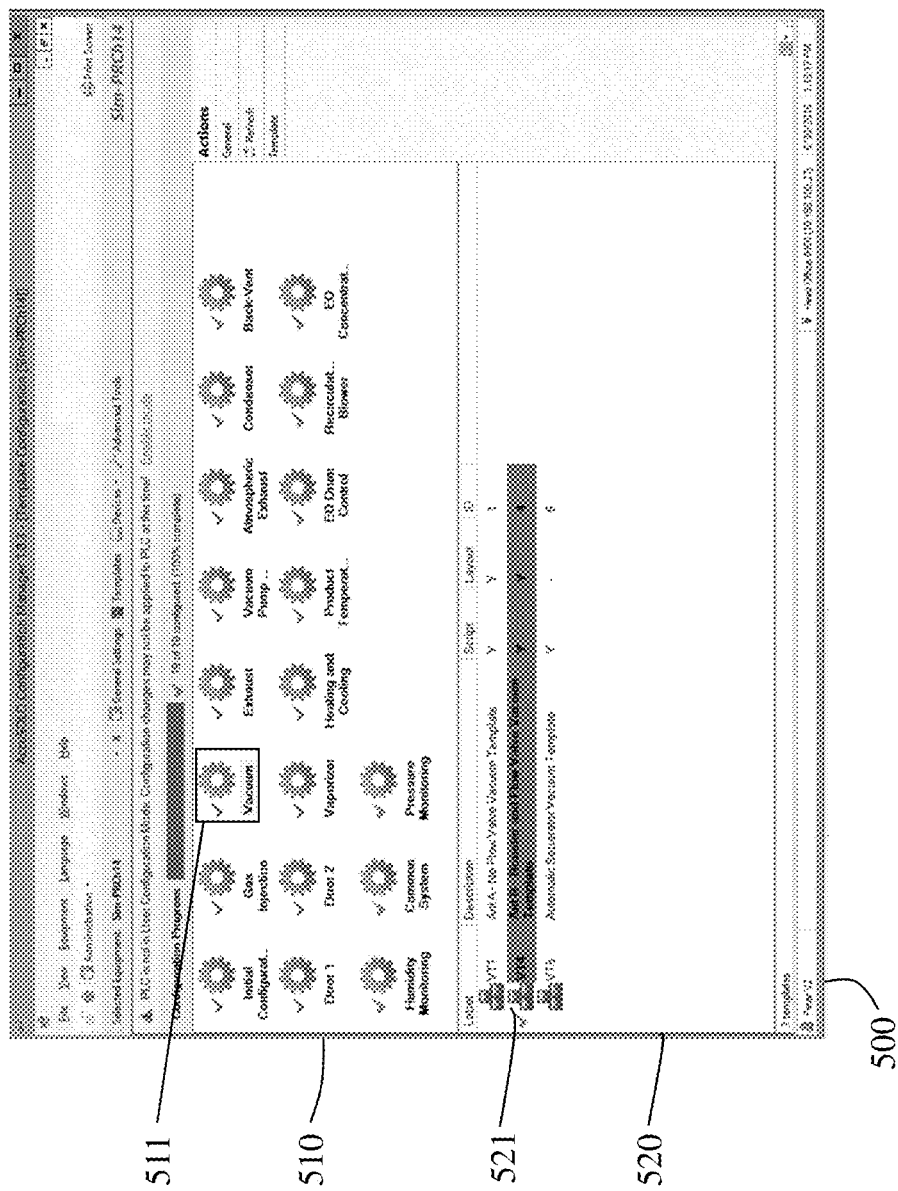
FIG. 5 is an illustration of an exemplary graphical user interface according to at least one embodiment of the present disclosure.

Reference is now made to FIG. 5, which illustrates a graphical user interface (GUI) for configuring templates according to at least one embodiment of the present disclosure.

In the embodiment of FIG. 5, GUI 500 shows 19 different template types in upper window 510. However, FIG. 5 is provided merely as an example and other embodiments may include fewer than 19, or more than 19 template types.

As seen in FIG. 5, the template types correspond to commonly used subsystems, such as for example, gas injection, vacuum, exhaust, vacuum pump, atmospheric exhaust, condenser, back vent, door, vaporizer, heating and cooling, and the like. GUI 500 allows a user to configure each template type, by selecting a template from a list of templates associated to the template type.

For example, in FIG. 5, template type 511, labeled "Vacuum", is selected by the user. In the embodiment of FIG. 5, selection of a template type in upper window 510 displays a list of available template for the selected template type in lower window 520. In this case, the list of available templates consists of templates labeled "VT1", "VT4", and "VT5", respectively. This list is provided for illustrative purposes only, and is in no way limiting to the present disclosure. As can be seen from FIG. 5, template 521, labeled "VT4" has been selected by the user, and therefore the template type 511, for the Vacuum device has been configured to template 521, corresponding to the VT4 vacuum.

According to at least some embodiments, the selected template may be further configured by allowing a user to select template options for the selected template.

Figure 6:
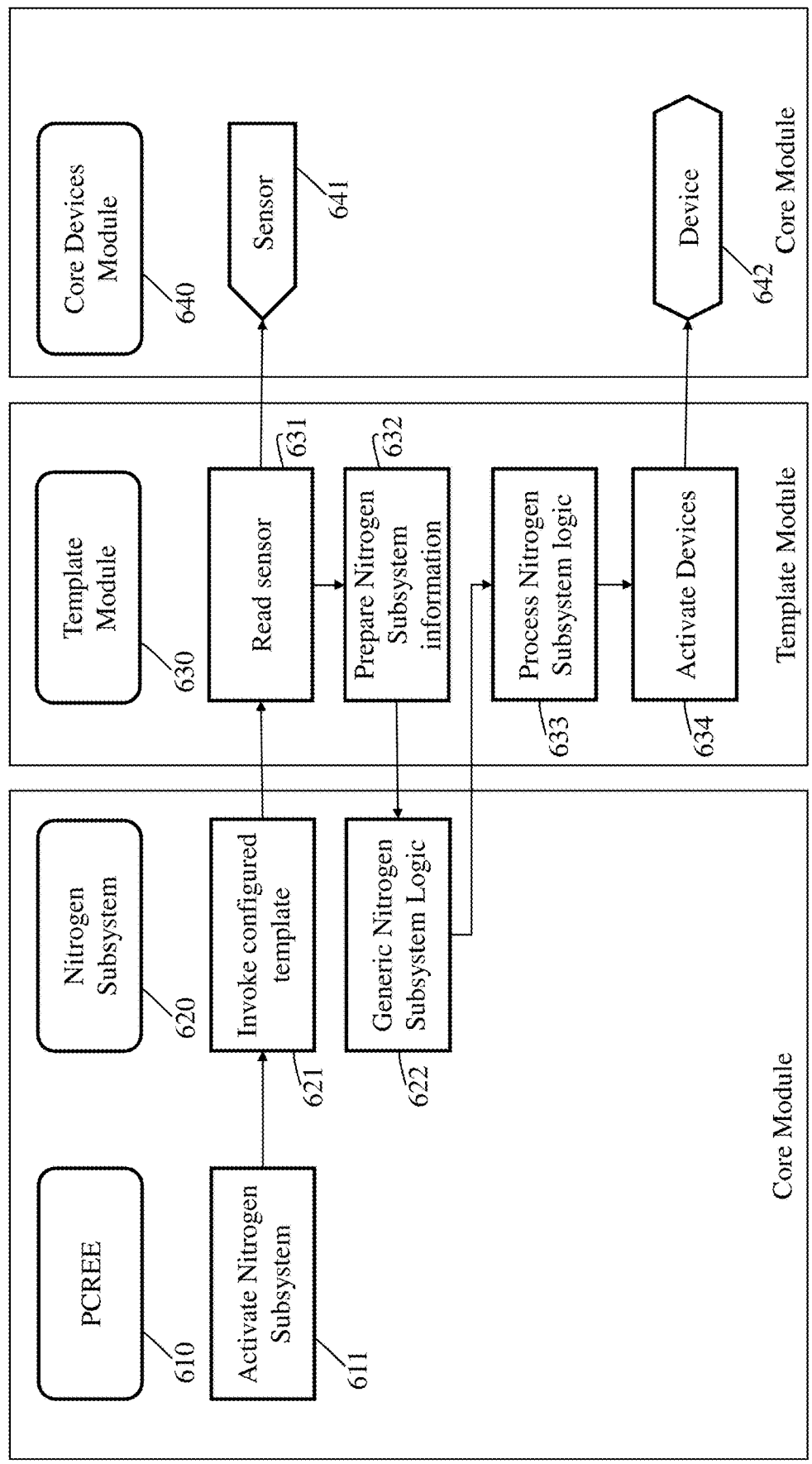
FIG. 6 is a conceptual diagram of a program flow for controlling a sterilization chamber according to at least one embodiment of the present disclosure.

Reference is now made to FIG. 6, which illustrates an exemplary program flow according to at least one embodiment of the present disclosure. For comparison purposes, the program flow of FIG. 6 illustrates a program similar to that of FIG. 3.

In FIG. 6, the process starts at block 611, where the PCREE 610 activates the Nitrogen Subsystem 620. This is occurring within the execution of a sterilization cycle, and the Nitrogen Subsystem is used for illustrative purposes only.

As discussed above, Nitrogen Subsystem 620 is activated by PCREE 610 using a standard interface. Upon being activated, Nitrogen Subsystem 620 checks which template is configured and invokes the configured template at block 621. Notably, this operation by Nitrogen Subsystem 620 is the same regardless of the hardware configuration of the sterilization chamber being used, and the software may also be the same regardless of the hardware configuration being used.

Control then passes to Template Module 630, which executes the software associated to the configured template for Nitrogen Subsystem 620. Template Module 630 is specific to the hardware configuration of the sterilization chamber. This allows the high level functions which are common across all sterilization chambers to be executed by the same software, while segregating the hardware-specific software to where it is necessary.

Template Module 630 may be implemented as a single piece of software which is the same for any sterilization chamber, but which uses configuration data to ensure proper operation with the specific hardware of the sterilization chamber.

Alternatively, Template Module 630 may include software for a plurality of device models and sensor models. During execution only the software for the device models and sensor models corresponding to the chamber configuration is invoked, as determined by the selected template. Specifically, the configuration data may consist of a template identifier, and the template identifier may be used to select software to execute for invoking the appropriate devices and sensors.

Returning to FIG. 6, the Template Module 630 reads a sensor at block 631. As described above, Template Module 630 has access to configuration data, such as a template identifier, which allows it to communicate effectively with the sensor.

Then, at block 632, Template Module 630 prepares information for Nitrogen Subsystem 620. For example, this information may consist of the sensor reading taken by Template Module 630 at block 631, presented in a standard format that is understandable for Nitrogen Subsystem 620. However, other types of information may be provided and the present disclosure is not so limited.

The process then returns to Nitrogen Subsystem 620 which performs logical operations at block 622 as required based on the information prepared at block 632.

As shown by block 633, the process returns to Template Module 630 which performs logical operations based on the configuration data, such as a template identifier. The process goes on to block 634 in which the appropriate devices are activated, or deactivated. In at least one embodiment, the decision to activate or deactivate the device may be based on the logic processed at block 633. As discussed above, Template Module 630 is capable of interacting with the device correctly based on the configuration data for Nitrogen Subsystem 620.

As seen in FIG. 6, execution of a sterilization cycle according to the present disclosure uses software which is independent of the manufacturer or model of the sterilization chamber. More specifically, the software executed by the PLC is the same across all chambers, and uses configuration data to ensure proper operation with the chamber in use. High level software interacts with a number of subsystems using a standard interface, and each subsystem uses the configuration data to ensure compatibility with the hardware of the sterilization chamber.

The present disclosure will be described with respect to a PLC however this is not intended to be limiting and the methods and techniques disclosed herein may be practiced using other types of computing devices as is known in the art.

Figure 7:
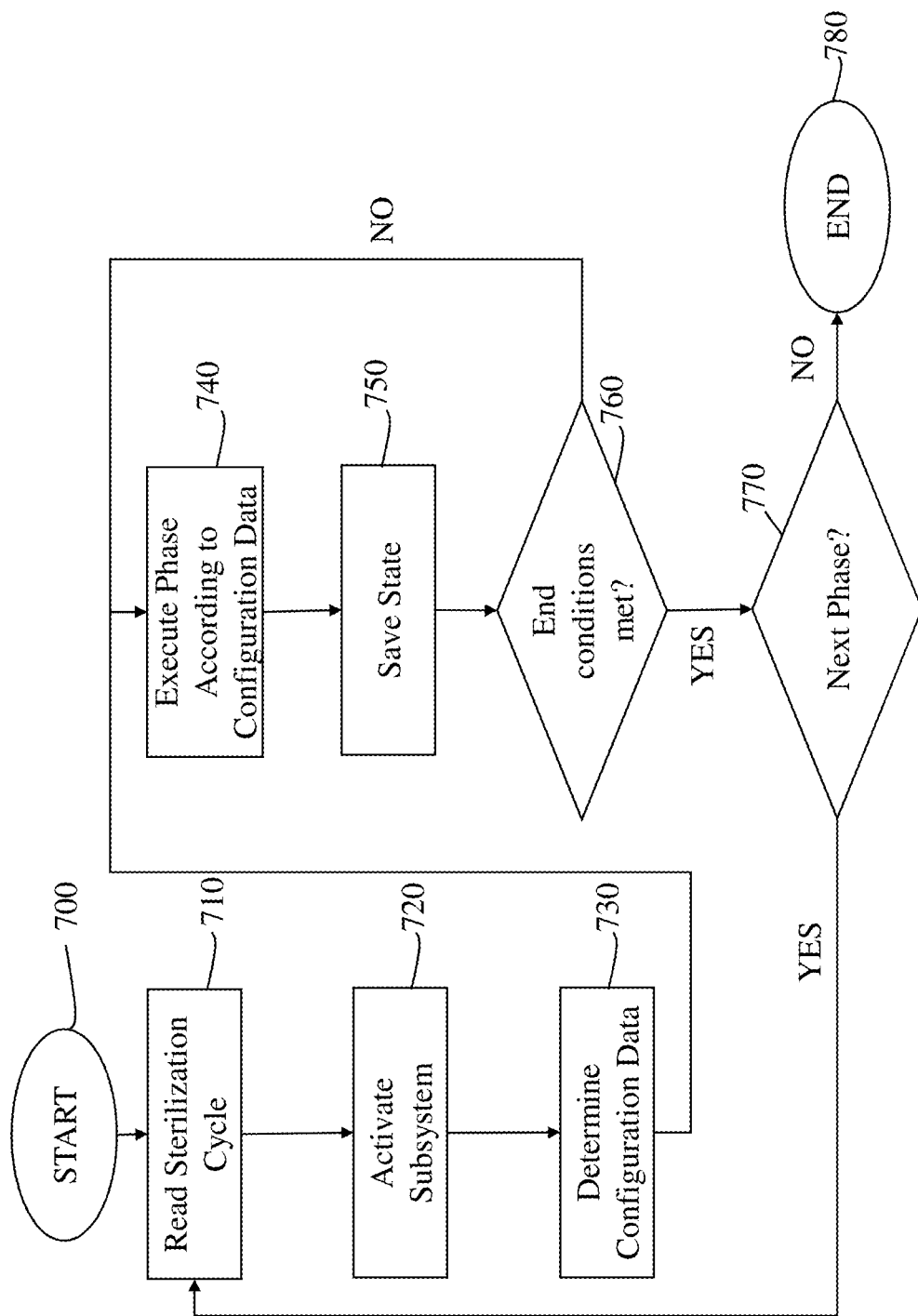
FIG. 7 is a flow diagram for execution of a sterilization cycle according to at least one embodiment of the present disclosure.

Reference is now made to FIG. 7, which illustrates the execution of a sterilization cycle according to at least one embodiment of the present disclosure.

The process starts at block 700, and proceeds to block 710, where the sterilization cycle is read. As discussed above, sterilization chambers execute sterilization cycles according to strict specifications to achieve a required level of sterility for the product within the chamber. Sterilization cycles include a series of phases, with each phase having associated end conditions. Each phase is performed until the end conditions are met within the chamber, at which point the next phase is performed. A sterilization cycle may consist of a file in which data representing phases and their corresponding end conditions are stored. However, the present disclosure is not so limited. According to at least one embodiment, block 710 is performed by the PREE.

The process moves on to block 720 where the PREE invokes an appropriate subsystem based on the current phase. For example, the current phase may require the injection of steam at a specified temperature and pressure, for a given time period. The PREE then invokes the steam subsystem using a standard interface as discussed above, along with the appropriate parameters to achieve the temperature, pressure, and time required by the sterilization cycle. As a further example, the current phase may require the evacuation of steam from the chamber. In this case, the PREE invokes the vacuum subsystem using a standard interface. Other examples would be apparent to those skilled in the art.

Upon being activated, the subsystems determine their configuration data at block 730. In at least one embodiment, the configuration data consists of a template identifier identifying a selected template from a plurality of predetermined templates, corresponding to logic which is specifically tailored for the hardware configuration of the subsystem. In at least another embodiment, the configuration data comprises a plurality of parameters. However, in either case, the configuration data allows the subsystem to properly interact with the specific hardware configuration of the sterilization chamber.

The process moves on to block 740, where the subsystem performs the relevant tasks for the current phase according to the configuration data. As discussed above, the configuration data allows the subsystem to interact with the specific hardware configuration of the sterilization chamber. For example, a series of devices may be involved in evacuation of gas from the chamber. The configuration data may provide information about dependencies between these devices (e.g. a time delay between starting the vacuum pump and opening the evacuation block valve). The configuration data ensures that chamber devices associated with the subsystem are able to properly execute required operations within each phase of the sterilization cycle by providing information about the hardware configuration of the sterilization chamber and also ensure that the software operation can be easily adapted to a plurality of chambers with different hardware arrangement.

In at least some other embodiments, the configuration data identifies specific routines to be executed for actuating a device or for taking a reading from a sensor, based on a selected template from a plurality of templates.

After the subsystem has performed the relevant tasks for the current phase at block 740, the process moves on to block 750 where state information is saved. The state information is saved remotely so that it is accessible even in the case of PLC failure. In at least some embodiments, the state information is also saved at regular intervals.

In at least one embodiment, at block 760, it is determined whether end conditions are met. Parameter values for end conditions are defined in the specification cycle. When the end conditions are met, the PREE determines that the next phase of the sterilization cycle may be performed. If the end conditions are not met, the process returns to blocks 740 and block 750 and save the state data again, until the end conditions are met. If the end conditions are met, the process moves on to block 770, where it is determined what is the next phase to perform in the current sterilization cycle.

If there are further phases, the process returns to block 710. Otherwise, the process moves on to block 780, and ends.

Therefore, regardless of the chamber model being used, or the sterilization cycle being executed, the same program may be used on any chamber.

Figure 8:
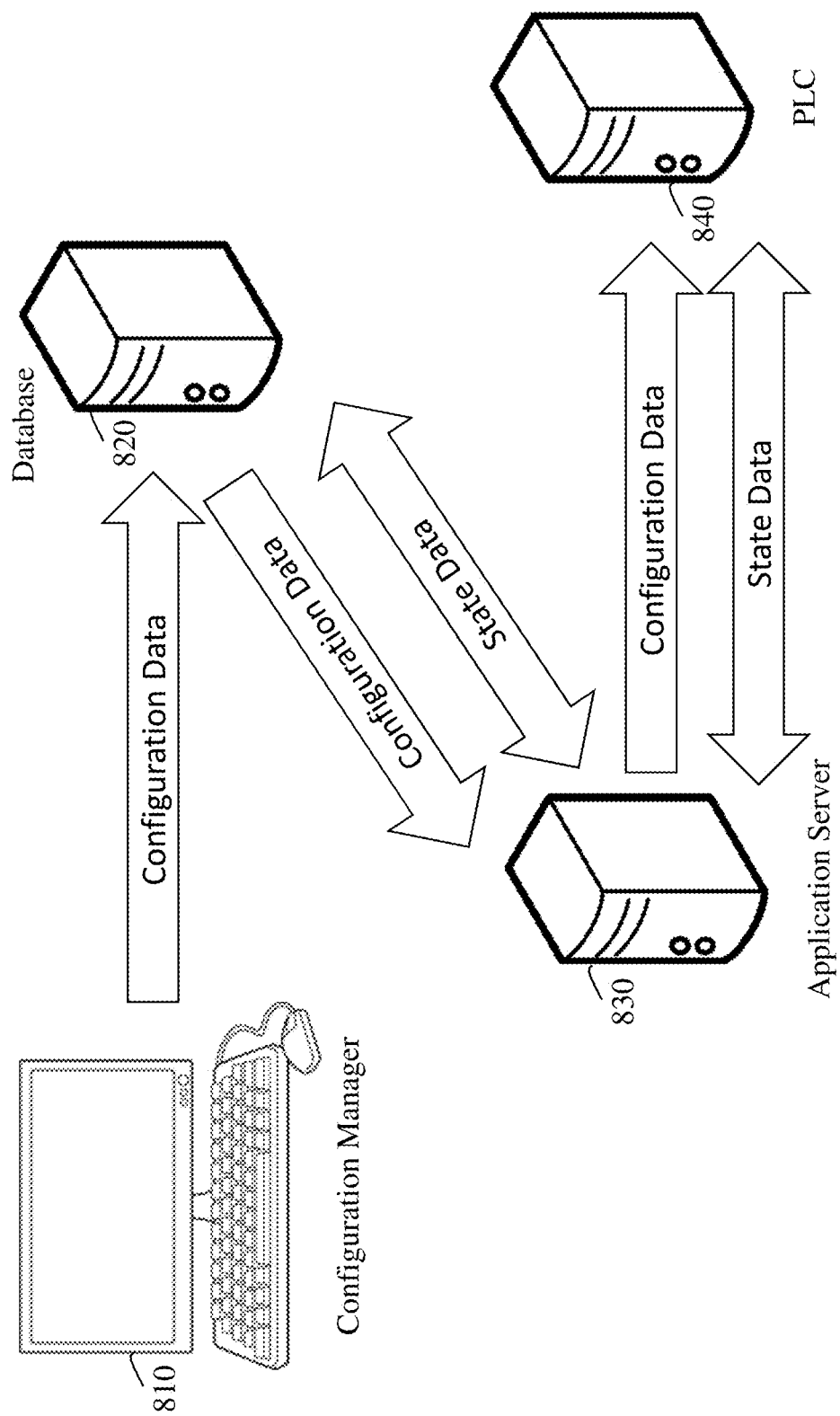
FIG. 8 is a diagram of a system for configuring a chamber according to at least one embodiment of the present disclosure.

Reference is now made to FIG. 8, which illustrates one system for providing configuration data during execution of a sterilization cycle.

A configuration manager 810 is provided on a computer terminal. Configuration manager 810 provides a user interface for allowing a user to enter configuration data for a specific chamber, and for storing the configuration data on database 820. According to at least one embodiment, the user interface provided by configuration manager 810 is the user interface illustrated in FIG. 5. For example, configuration manager 810 allows a user to select a template from a plurality of template option. In another embodiment, configuration manager 810 allows a user to enter values for a plurality of parameters for each subsystem. Configuration manager 810 may also export configuration data in a portable format, such as eXtensible Markup Language (XML) for use in a different chamber having the same hardware configuration.

Database 820 receives the configuration data from configuration manager 810, and stores it until it is used to configure a generic PLC program to control/operate a specific chamber hardware configuration.

In the system specifically illustrated in FIG. 8, there is provided an application server 830 that serves as an intermediary between PLC 840 and database 820.

During execution of a sterilization cycle, the PLC maintains state information. This state data may be retrieved by the application server 830 and saved to the database 820 at various intervals.

Figure 9:
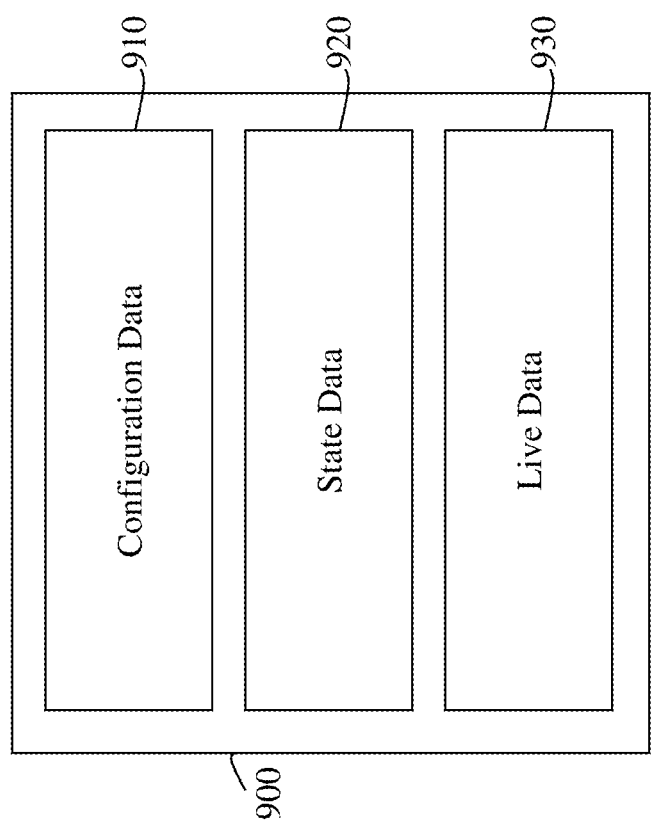
FIG. 9 is a conceptual diagram of data separation according to at least one embodiment of the present disclosure.

Reference is now made to FIG. 9, which shows how different types of data may be separated on the PLC. During execution of a sterilization cycle, the PLC maintains various types of data. Traditionally, all data maintained by the PLC is treated uniformly and there is no formal separation of data. Instead, data maintained by the PLC is traditionally stored within the same memory devoted to the program executing on the PLC.

The above is illustrated in FIG. 9, which shows the data 900 separated into three separate categories.

Configuration data 910 contains the configuration data for the current chamber. As discussed above, this data allows the PLC to run a single program for any chamber, regardless of the make or model of the chamber. In at least some embodiments, the configuration data may include a selected template for each template type. Each template type is responsible for controlling one or more subsystems. In another embodiment, the configuration data may further include additional parameters for the selected template. In another embodiment, the configuration data does not include template identifiers but instead consists of a plurality of parameters for each subsystem.

The configuration data may further include configuration data for the chamber, and include parameters for minimum and maximum pressure, a model identifier, an equipment identifier, and the like.

State data 920 is data that represents the state of the sterilization cycle currently in execution, as discussed above. The state data may include any data that allows an interrupted cycle to be resumed at the correct point. For example, the state data may include the last completed phase of the sterilization cycle, or the calibration parameters of sensors such as the slope and offset that is used in measured value calculations. Other types of state data would be apparent to those skilled in the art. State data may be saved for a chamber, for every subsystem within the chamber, and for every device in the subsystem. For example, state data for a valve may hold a value representing the amount a time a valve has been opened for. In a further embodiment, the state data includes state data for devices and sensors. For example, state data may specify how long a valve has been opened.

Live data 930 includes all data that is stateless and resolved in real time. In at least one embodiment, the live data is simply the data that is not configuration data or state data.

As seen in FIG. 9, configuration data 910, state data 920, and live data 930 are segregated in memory. This allows to properly resume a sterilization cycle if a cycle is interrupted because of a PLC failure or other reason. More specifically, the PLC may be programmed to resume an interrupted cycle by having an application server write the saved state data into the segregated memory area of the PLC reserved for the state data. This data is also recovered automatically when a new version of the control software is downloaded to the controller. The previously saved configuration and state data is restored and merged with the new program. This can take place even if the data structure of the new program has changes from the previous version of the program.

For example, if a new version of the chamber control software expects new chamber states which did not exist in prior versions, the new chamber states may be set to default values. The new version of the software should be able to function properly with the default value, considering that this chamber state did not exist in prior versions of the software. In some cases, the new version of the chamber control software will have fewer chamber states than prior versions. If that is the case, the chamber states saved in a database from a previous software version are not taken in consideration by the new software version, and are not written to the memory area dedicated to state data. The new version of the software may still function properly as it does not need those chamber states. This provides an improvement over the prior art, as it allows to restore a previous state regardless of whether the memory configuration of the chamber control software has changed.

Therefore, according to the present disclosure, in both the cases of a catastrophic PLC failure and a software update, only generic software is installed on a chamber PLC, and the generic software is customized with configuration data to support the hardware configuration of the chamber. This greatly simplifies maintenance and operation of a large number of sterilization chambers having different hardware configurations.

Figure 10:
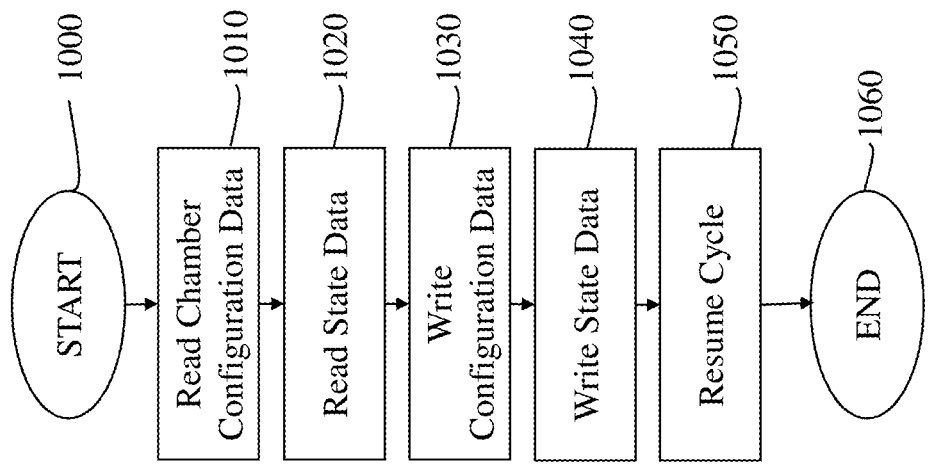
FIG. 10 is a flow diagram for recovery of an interrupted sterilization cycle according to at least one embodiment of the present disclosure.

Reference is now made to FIG. 10 which illustrates the process for recovering an interrupted cycle according to at least one embodiment of the present disclosure. The process of FIG. 10 is performed by a computing device which is external to the chamber. For example, in at least one embodiment the process of FIG. 10 is performed by a device such as the application server 830 illustrated in FIG. 8.

The process starts at block 1000 and proceeds to block 1010, in which the chamber configuration data is read. This data may be read from a database as discussed above, or an application server.

The process then moves on to block 1020, in which state data for the chamber is read. As discussed above, state data maybe saved at regular intervals during execution of a sterilization cycle, or after every phase of a cycle. Therefore, if a cycle has been previously interrupted for reasons such as PLC failure, the last saved state data may be retrieved from a database by an application server.

The process then moves on to block 1030 in which configuration data is written into the PLC, and block 1040 in which state data is written into the PLC. The configuration data is written to the PLC memory reserved for configuration data, and the state data is written to the PLC memory reserved for state data. Once the PLC has the configuration data for a chamber, the state data for a previously interrupted cycle, and the state of each device restored, the PLC may resume the execution of the previously interrupted cycle at block 1050. In at least one embodiment, an application server sends a command to the chamber PLC to resume the cycle. In at least another embodiment, the cycle is resumed by a human operator of the sterilization chamber.

The teachings of the present disclosure may be implemented by using hardware only or by using a combination of software and hardware. Software or other computer executable instructions for implementing one or more embodiments, or one or more portions thereof, may be stored on any suitable computer readable storage medium. The computer readable storage medium may be a tangible or in transitory/non-transitory medium such as optical (e.g., CD, DVD, Blu-Ray, etc.), magnetic, hard disk, volatile or non-volatile, solid state, or any other type of storage medium known in the art.

Additional features and advantages of the present disclosure will be appreciated by those skilled in the art.

The structure, features, accessories, and alternatives of specific embodiments described herein and shown in the Figures are intended to apply generally to all of the teachings of the present disclosure, including to all of the embodiments described and illustrated herein, insofar as they are compatible. In other words, the structure, features, accessories, and alternatives of a specific embodiment are not intended to be limited to only that specific embodiment unless so indicated.

Furthermore, nothing herein is intended as an admission of prior art or of common general knowledge.

The invention claimed is:

1. A computing device for operating a sterilization chamber having a plurality of subsystems, comprising:
   a processor;
   memory; and
   a communication subsystem;
wherein the processor, memory, and communication subsystem cooperate to:
   receive configuration data for the chamber at the computing device, the configuration data indicating a template and template parameters for each subsystem of the plurality of subsystems, the template defining software for controlling a device or a sensor of a corresponding subsystem;
   read phase information from a sterilization cycle specification; and
   invoke a subsystem of the sterilization chamber corresponding to the phase information using a standard interface of the subsystem;
wherein the subsystem executes a phase using the phase information and the configuration data.

2. The computing device of claim 1, wherein the template is selected from a plurality of templates for each subsystem.

3. The computing device of claim 1, wherein state data is stored in a first segregated area of the memory.

4. The computing device of claim 3, wherein the processor, memory, and communication subsystem further cooperate to transmit the state data to a remote storage device.

5. The computing device of claim 4, wherein said transmitting occurs after at least one of:
   a time interval; and
   the execution of the phase.

6. The computing device of claim 5, wherein the configuration data is stored in a second segregated area of the memory.

7. The computing device of claim 4, wherein the processor, memory, and communication subsystem further cooperate to:
   retrieve the state data from the external storage device;
   store the state data in the first segregated memory area.

8. The computing device of claim 7, wherein the processor, memory, and communication subsystem further cooperate to:
   read the state data from the first segregated memory area;
   determine a next phase to be executed based on the state data.

9. The computing device of claim 1, wherein the subsystem is selected from a group comprising a gas injection subsystem, a vacuum subsystem, an exhaust subsystem, a vacuum pump subsystem, an atmospheric exhaust subsystem, a condenser subsystem, a back-vent subsystem, a door subsystem, and a heating and cooling subsystem.

10. The computing device of claim 1, wherein the device is selected from the group comprising a valve and a pump, and the sensor is selected from the group comprising a temperature sensor, a pressure sensor, and a humidity sensor.

11. The computing device of claim 1, wherein the computing device is programmed with software for a plurality of device and sensor models, and wherein the selected template identifies at least one of the plurality of device and sensor models.

12. The computing device of claim 1, wherein the sterilization chamber is an Ethylene Oxide (EtO) chamber.

13. The computing device of claim 1, wherein the computing device is a Programmable Logic Controller (PLC).

14. The computing device of claim 1 wherein the configuration data is received from an external storage device or application server.

15. The computing device of claim 1, wherein the configuration data is in eXtensible Markup Language (XML) format.

* * * * *